US006011013A

United States Patent [19]
Carr et al.

[11] Patent Number: 6,011,013
[45] Date of Patent: Jan. 4, 2000

[54] CONTRACEPTIVE COMPOSITIONS AND METHODS

[75] Inventors: Daniel W. Carr, Portland, Oreg.; Srinivasan Vijayaraghavan, Kent, Ohio

[73] Assignee: Oregon Health Sciences University, Portland, Oreg.

[21] Appl. No.: 09/100,789

[22] Filed: Jun. 18, 1998

Related U.S. Application Data

[60] Provisional application No. 60/050,314, Jun. 20, 1997.
[51] Int. Cl.⁷ .......................... A61K 38/10; A61K 38/16; C07K 7/08; C07K 14/00
[52] U.S. Cl. .............................. 514/13; 514/14; 530/325; 530/326; 530/327
[58] Field of Search ........................ 514/14, 13; 530/327, 530/326, 325

[56] References Cited

U.S. PATENT DOCUMENTS 5,229,423  7/1993  Rubenstein ............................ 514/588

OTHER PUBLICATIONS

Eichholtz, et al., "A Myristoylated Pseudosubstrate Peptide, a Novel Protein Kinase C Inhibitor" J. Biol. Chem. 1993, 268(3), 1982.
Vijayaraghavan, et al., "Protein Kinase A–anchoring Peptides Arrest Mammalian Sperm Motility" J. Biol. Chem. 1997, 272(8), 4747.
Garg, et al., "Synergistic Spermicidal Activity of Neem Seed Extract, Reetha Saponins and Quinine Hydrchloride" Contraception 1994, 50, 185.
Bourinbaiar, A.S. and Lee–Huang, S., Comparative In Vitro Study of Contraceptive Agents with Anti–HIV Activity: Gramicidin, Nonoxynol–9, and Gossypol, *Contraception* 49: 131–137 (1994).
Carr, D.W., and Acott, T.S., The Phosphorylation of a Putative Sperm Microtubule–Associated Protein 2 (MAP2) Is Uniquely Sensitive to Regulation, *Biology of Reproduction* 43:795–805 (1990).
Carr et al., Interaction of the Regulatory Subunit (RII) of cAMP–Dependent Protein Kinase with RII–Anchoring Proteins Occurs through Amphipathic Helix Binding Motif, *The Journal of Biological Chemistry* 266:14188–14192 (1991).
Carr et al., Association of the Type II cAMP–Dependent Protein Kinase with a Human Thyroid RII–Anchoring Protein, *The Journal of Biological Chemistry* 267:13376–13382 (1992).
Carr et al., Localization of the cAMP–Dependent Protein Kinase to the Postsynaptic Densities by A–Kinase Anchoring Proteins, *The Journal of Biological Chemistry* 267:16816–16823 (1992).
Carr et al., Follicle–Stimulating Hormone Regulation of A–Kinase Anchoring Proteins in Granulosa Cells, *The Journal of Biological Chemistry* 268:20729–20732 (1993).
Garg et al., Synergistic Spermicidal Activity of Neem Seed Extract, Reetha Saponins and Quinine Hydrochloride, *Contraception* 50:185–190 (1994).

d'Oro et al., Barrier Methods of Contraception, Spermicides, and Sexually Transmitted Diseases: A Review, *Genitourin Med* 70:410–417 (1994).
Eichholtz et al., A Myristoylated Pseudosubstrate Peptide, a Novel Protein Kinase C Inhibitor, *The Journal of Biological Chemistry* 268:1982–1986 (1993).
Ezzel, C., Sperm–Stoppers: Researchers Target the Sperm Cell Membrane in Male Contraceptives, *The Journal of NIH Research* 7:43–47 (1995).
Johnson et al., Voltage–Dependent Potentiation of L–type Ca2+ Channels in Skeletal Muscle Cells Requires Anchored cAMP–Dependent Protein Kinase, *Proc. Natl. Acad. Sci. USA* 91:11492–11496 (1994).
Lin et al., Characterization of S–AKAP84, a Novel Developmentally Regulated A Kinase Anchor Protein of Male Germ Cells, *The Journal of Biological Chemistry* 270:27804–27811 (1995).
Liotta et al., A Synthetic Tris–Sulfotyrosyl Dodecapeptide Analogue of the Insulin Receptor 1146–Kinase Domain Inhibits Tyrosine Dephosphorylation of the Insulin Receptor in Situ, *The Journal of Biological Chemistry* 269:22996–23001 (1994).
Meyer et al., Teratogenicity and in Vitro Mutagenicity Studies on Nonoxynol–9 and –30, *Pharmacology & Toxicology* 62:236–238 (1988).
Mochly–Rosen, D., Localization of Protein Kinases by Anchoring Proteins: A Theme in Signal Transduction, *Science* 268:247–251 (1995).
Rosenmund et al., Anchoring of Protein Kinase A is Required for Modulation of AMPA/Kainate Receptors on Hippocampal Neurons, *Nature* 28:853–856 (1994).
Vijayaraghavan et al., Disruption of PKA Anchoring Alters Calcium Homeostasis and Arrests Sperm Motility (Abstract), in Program for the Twenty–Ninth Annual Meeting of the Society for the Study of Reproduction meeting in London, Ontario, Canada, Jul. 27–30 (1996).
Vijayaraghavan et al., Protein Kinase A–Anchoring Inhibitor Peptides Arrest Mammalian Sperm Motility, *Journal of Biological Chemistry* 272:4747–4752 (1997).

*Primary Examiner*—Michael P. Woodward
*Assistant Examiner*—Anish Gupta
*Attorney, Agent, or Firm*—Klarquist Sparkman Campbell Leigh & Whinston, LLP

[57] ABSTRACT

The present invention includes a pharmaceutical composition having an effective contraceptive amount of a synthetic peptide that includes an amphipathic α-helix domain that binds to an RII subunit of protein kinase A, and competitively inhibits the binding of protein kinase A to sperm A kinase anchoring proteins. Particular disclosed synthetic peptides having this activity include s-Ht31: N-Stearate-DLIEEAASRIVDAVIEQVKAAGAY (SEQ ID No. 9), s-Ht31-P: N-Stearate-DLIEEAASRPVDAV PEQVKAA-GAY (SEQ ID No. 10), and s-AKAP79: N-Stearate-YETLLIETASSLVKNAIQLSIE (SEQ ID No. 11). The invention also includes methods of inhibiting sperm motility, by exposing them to an effective amount of the peptide, for example by placing the pharmaceutical composition (such as a suppository, foam, cream, or gel) in the vagina.

14 Claims, No Drawings

CONTRACEPTIVE COMPOSITIONS AND METHODS

RELATED APPLICATION DATA

This case claims priority from U.S. Provisional Patent Application No. 60/050,314, filed Jun. 20, 1997.

ACKNOWLEDGEMENT

The inventors' laboratory was supported in part by grant nos. R29HD32508 and HD30908-02 from the National Institutes of Health. The United States government may have rights in this invention.

FIELD OF THE INVENTION

This invention pertains to contraceptive compositions, particularly compositions that affect sperm motility.

BACKGROUND OF THE INVENTION

Signal transduction enzymes such as protein kinases and phosphatases play pivotal roles in mediating cellular responses to a wide variety of stimuli. These enzymes are often targeted to specific substrates or cellular compartments through their interaction with cellular "anchoring proteins" (Hubbard and Cohen, *Trends Biochem. Sci.* 18:172–177, 1993). This anchoring or compartmentalization is thought to be critical in determining the specificity of response for a particular stimulus (Scott and Carr, *News Physiol. Sci.* 7:143–148, 1992; Rubin, *Biochim. Biophys. Acta* 1224:467–479, 1994; Mochly-Rosen, *Science* 268:247–251, 1995). Anchoring of cyclic AMP (cAMP)-dependent protein kinase (PKA or A-kinase) is accomplished by the binding of the regulatory subunit (R) to an amphipathic helix-binding motif located within A-kinase anchoring proteins (AKAPs) (Carr et al., *J. Biol. Chem.* 266:14188–14192, 1991).

Synthetic peptides containing an amphipathic helix domain are able to competitively disrupt PKA binding to AKAPs (Carr et al., *J. Biol. Chem.* 267:13376–13382, 1992). Microinjection of these anchoring inhibitor peptides (AIPs) into neurons or skeletal muscle cells disrupts PKA anchoring and PKA modulation of glutamate receptor channels (Rosenmund et al., *Nature* 368:853–856, 1994) and voltage-gated calcium channels (Johnson et al., *Proc. Natl. Acad. Sci. USA* 91:11492–11496, 1994). However, microinjection is impractical for normal pharmaceutical applications.

SUMMARY OF THE INVENTION

PKA anchoring has been discovered to be a key factor in the regulation of sperm motility. AIPs inhibit sperm motility by disrupting PKA anchoring and thus are useful for contraceptive purposes.

The present invention provides cell-permeable AIPs, e.g., AIPs that include a fatty-acid moiety attached to a terminal amino acid, e.g., a stearate or myristate group. Also provided are pharmaceutical compositions that include an effective dose of an AIP, preferably a cell-permeable AIP. Such pharmaceutical compositions can also include other active ingredients, excipients, diluents, etc. For contraceptive purposes, for example, an AIP or mixture of AIPs can be used in combination with another contraceptive substance, e.g., a spermicidal agent such as nonoxynol-9.

METHODS AND MATERIALS

Example 1 shows the identification of PKA subunits and AKAPs in mammalian sperm was performed. Sperm from bovine (B), human (H) and monkey (M), were lysed and the proteins were separated by SDS-PAGE and analyzed by Western blotting for regulatory subunits of PKA (RI$\beta$, RII$\alpha$, or RII$\beta$) using isoform specific antibodies, or for AKAPs using $^{32}$P-labeled RII$\alpha$ or RII$\beta$. Identification of PKA isoforms in three different species of sperm using four different antibodies. Bovine caudal epididymal sperm were lysed and separated into supernatant (S) or pellet (P) fractions by centrifugation at 16,000×g and probed using anti-RII$\alpha$, anti-RII$\beta$ and anti-RI$\beta$ antibodies. A single predominant AKAP was detected in bovine, human, and monkey sperm using either RII$\alpha$ or RII$\beta$ as a probe. The bovine and human AKAPs had relative molecular weights of 110 kDa and the monkey AKAP was approximately 115 kDa. The overlay assay also detects the endogenous RII isoforms accounting for the bands observed at 55 kDa. Disruption of RII binding to sperm AKAPs by anchoring inhibitor peptides. RII overlays were performed in the absence (lane 1) or presence of 20 $\mu$M Ht31 peptide, s-Ht31 peptide or s-Ht31-P peptide (lanes 2, 3 or 4, respectively). Addition of the peptides inhibited RII binding to AKAP110 by 100%, 85% and 0%, respectively, as determined by densitometric scanning analysis.

Example 2 shows that anchoring inhibitor peptides arrest bovine sperm motility in a time- and dose-dependent manner. (A) Sperm were incubated in buffer A containing s-Ht31 at 5 $\mu$M (circle), 10 $\mu$M (square) or 50 $\mu$M (diamond) or a control peptide, S-Ht31-P at 50 $\mu$M (cross). Motility was assessed at the times indicated by computer-automated sperm motility analysis (CASMA) as described in Experimental Procedures. (B) Sperm were incubated for 5 min in buffer A containing increasing concentrations of S-Ht31 (diamonds) or control peptide S-Ht31-P (triangle) and motility was assessed.

Example 3 shows reactivation of S-Ht31-inhibited motility in the presence of calcium and bicarbonate. (A) Bovine caudal epididymal sperm were suspended in buffer A supplemented with 2 mM calcium (+Calcium) or 2 mM EGTA (–Calcium). Motility was assessed by CASMA at 5, 30 and 60 min following addition of either water (control) or 10 $\mu$M s-Ht31. (B) Sperm were incubated in buffer A containing 2 mM calcium and 50 mM bicarbonate (where indicated). Motility was assessed at 5, 30 and 60 min following addition of either water (control) or 10 $\mu$M s-Ht31.

Example 4 shows the effect of the protein kinase inhibitor N-[2-(p-bromocinnamylamino)ethyl]-5-isoquinoline-sulfonamide (H-89) on sperm motility and PKA activity from control sperm and sperm activated by 2-chloro-2-deoxyadenosine (CDA). (A). Bovine caudal and caput sperm were incubated in buffer A in the presence or absence of 50 $\mu$M CDA and/or 50 $\mu$M H-89. When sperm were treated with both CDA and H-89, the H-89 was added 15 min prior to CDA. Motility was assessed by CASMA at 15 min following treatment. (B) Bovine sperm were incubated as described for A and then assessed for PKA activity. Where indicated, 10 $\mu$M cAMP was added to the PKA assay.

Example 5 shows the effect of s-Ht31, s-AKAP79, and s-Ht31-P on the motility of bovine sperm. Sperm were incubated for 5 min in buffer A containing increasing concentrations of s-Ht31 (diamonds), S-AKAP79 (squares) or control peptide S-Ht31-P (triangles) and motility was assessed.

Example 6 shows the effect of s-AKAP79 on the motility of monkey-ejaculate sperm at 5 min (dark gray bar) and 20 min (dark gray bar). Increasing concentrations of S-AKAP79 were added to neat monkey semen and incubated at 37° C. Motility was assessed at 5 and 30 min.

Example 7 shows the effect of s-Ht31 on the motility of monkey semen and swim-up sperm. Monkey sperm, either neat semen or semen collected after swim-up analysis, were incubated with no addition (Control) (open bar), 50 μM S-Ht31 (solid bar), 2.5 mM EGTA (hatched bar) or 2.5 mM EGTA plus 50 μM S-Ht31 (dotted bar). Motility was assessed after 15 min.

Example 8 shows the effect of s-Ht31 on the motility of human-ejaculate swim-up sperm. Human sperm collected after swim-up analysis, were incubated for 15 min with no addition (Control), 100 μM S-Ht31, or 100 μM S-Ht31-P and assessed for motility.

DETAILED DESCRIPTION OF THE PREFERRED EMBODIMENTS

AIPs competitively disrupt PKA binding to AKAPs and cause loss of PKA modulation of cellular responses. It has been discovered that AIPs inhibit sperm motility in a time- and concentration-dependent manner.

The inhibition of sperm motility by an AIP (e.g., S-Ht31) is reversible, but only if calcium is present in the suspension buffer, suggesting a role for PKA anchoring in regulating cellular calcium homeostasis. Surprisingly, inhibition of PKA catalytic activity had little effect on basal motility or motility stimulated by agents previously thought to work via PKA activation. Thus, the interaction of the regulatory subunit of PKA with sperm AKAPs, independent of PKA catalytic activity, is a key regulator of sperm motility.

Cyclic AMP mediates the motility of sperm and a variety of other ciliated cells (Satir, *Modern Cell Biol.* 4:1–46, 1985; Tash, *Cell Motil. Cytoskel.* 14:332–339, 1989; Bedford and Hoskins, in *Marshall's Physiology of Reproduction*, Lamming, ed., pp. 379, Churchill Livingstone, New York, 1990). Increases in the level of this nucleotide are associated with development of motility in the epididymis (Bedford and Hoskins, in *Marshall's Physiology of Reproduction*, Lamming, ed., pp. 379, Churchill Livingstone, New York, 1990; Hoskins et al., *J. Reprod. Fertil.* 37:131–133, 1974). Cell-permeant cAMP analogs, cAMP phosphodiesterase inhibitors, and adenylyl cyclase activators all stimulate motility of sperm from several species (Garbers et al., *Biol. Reprod.* 7:132, 1972; Garbers et al., *Adv. Cyclic Nucleotide Res.* 9, 583–595, 1978; Hoskins, *Journal of Biological Chemistry* 248:1135–1140, 1973; Hoskins et al., *Biol. Reprod.* 13:168–176, 1975; Vijayaraghavan and Hoskins, *J. Cyclic Nucleotide Protein Phosphoryl. Res.* 10:499–510, 1985). The kinetic and metabolic responses to cAMP elevation occur within 5 to 10 minutes (Garbers et al., *Biol. Reprod.* 7:132, 1972; Garbers et al., *Adv. Cyclic Nucleotide Res.* 9:583–595, 1978).

Sperm lack nucleic-acid and protein-synthetic activity, thereby considerably reducing the possible range of targets of cAMP action. The highly polarized sperm cell has distinct subcellular structures easily distinguished at the light microscopic level. Immunogold staining indicates a predominant localization of type II PKA (RII) to the outer membrane of the mitochondria that spiral around the proximal flagella (Lieberman et al., *J. Cell Biol.* 107:1809–1816, 1988). A developmentally regulated sperm AKAP (AKAP-84) is also localized to sperm mitochondria (Lin et al., *J. Biol. Chem.* 270:27804–27811, 1995).

PKA anchoring is a key factor in the regulation of sperm motility. AIPs, but not PKA inhibitors, arrest sperm motility. Thus, the interaction of RII with AKAPs, but not PKA catalytic activity, has been discovered to be essential for sperm motility.

Most spermicidal agents in current use employ nonspecific toxic compounds (e.g., nonoxynol-9) that have adverse effects on cells lining the vaginal tract. AIPs are expected to have minimal side effects at concentrations that fully inhibit sperm motility.

Definitions and Methods

The following definitions and methods are provided to better define the present invention and to guide those of ordinary skill in the art in the practice of the present invention. Definitions of common terms may also be found in Rieger et al., *Glossary of Genetics: Classical and Molecular,* 5th edition, Springer-Verlag: New York, 1991; and Lewin, *Genes V,* Oxford University Press: New York, 1994. The standard one- and three letter nomenclature for amino acid residues is used.

"Anchoring Inhibiting Peptides". An anchoring inhibiting peptide or AIP is defined as a peptide that (1) possesses an ampiphatic α-helical structure; (2) binds to PKA; and (3) interferes with binding of PKA to an AKAP.

Subcellular localization of PKA is directed through the regulatory (R) subunit. There are two R subunit classes, RI and RII, which form the type I and type II holoenzymes, respectively. Type II PKA is present in all cells, whereas the tissue distribution of type I PKA is more restricted. Type II PKA localization is dictated by the association of RII with AKAPs. Tissue-specific AKAP localization has been detected by protein-blotting techniques or by fractionation on RII-Sepharose affinity columns.

All AKAPs identified to date contain an amphipathic helix domain that is responsible for RII binding (Carr et al., *J. Biol. Chem.* 266:14188–14192, 1991; Carr et al., *J. Biol. Chem.* 267:13376–13382, 1992; Carr et al., *J. Biol. Chem.* 267:16816–16823, 1992; Coghlan et al., *J. Biol. Chem.* 269:7658–7665, 1994; McCartney et al., *J. Biol. Chem.* 270:9327–9333, 1995). An ampipathic helix is an α-helix with opposing hydrophilic and hydrophobic faces orientated down the long axis of the helix. As discussed in the Example below, substantial disruption of the α-helical structure significantly reduces or eliminates AIP binding to RII.

The RII-binding amphipathic helix of an AKAP can be identified by a computer-aided secondary structure prediction method (Eisenberg et al., *Proc. Natl. Acad. Sci. USA* 81:140–144, 1984). A characteristic of the amphipathic helix motif of about 14 amino-acid residues is the ordered placement of alternating pairs of hydrophobic and hydrophilic amino acids within the linear sequence of a protein. In addition, each RII-anchoring protein contains acidic amino acids distributed over the hydrophilic face of the helix. In particular, a glutamic acid residue at position 3 is located within the first turn of the amphipathic helix of most wild-type AKAPs.

Preferably, the AIP includes an amino acid sequence that is identical to that of the RII-binding portion of a "native" (naturally-occurring or wild-type) AKAP. Additional amino-acid residues may be included, preferably at the amino-terminus or carboxy-terminus of the AIP, so as not to interfere with binding of the AIP to PKA.

Amphipathic helix sequences predicted to bind RII include, but are not limited to:

| | | |
|---|---|---|
| Ht 31 (494–507) | LIEEAASRIVDAVI | (SEQ ID No. 1) |
| MAP2 (87–100) | TAEEVSARIVQVVT | (SEQ ID No. 2) |
| AKAP 150 (429–442) | LIETASSLVKNAIQ | (SEQ ID No. 3) |
| AKAP 79 (392–405) | LIETASSLVKNAIE | (SEQ ID No. 4) |
| AKAP 95 (642–659) | EVAAEVLAEVITAAVKAV | (SEQ ID No. 5) |
| AKAP 100 (396–411) | IIDMASTALKSKSQ | (SEQ ID No. 6) |
| AKAP 220 (905–918) | LAEKIVAEAIEKAE | (SEQ ID No. 7) |
| AKAP84 (355–376) | VISEATEQVLATTVGKVAGRVC | (SEQ ID No. 8) |

The sequence of the RII-binding domain of a wild-type AKAP polypeptide, i.e., a "native" AIP sequence, can be modified by substituting a hydrophobic amino-acid residue with another hydrophobic residue or substituting a hydrophilic residue with another hydrophilic residue, for example. Preferably acidic residues are replaced with other acidic residues. Residues that lie outside the predicted amphipathic helix region of an RII-binding region of an AKAP may enhance RII binding by stabilizing the overall conformation of the region and are preferably included in the AIP sequence. As a result, AIPs that include additional sequences from the RII binding region of an AKAP flanking the helix-forming sequence are preferred. AIPs shorter than 14 amino-acid residues may also bind RII.

Suitable AIP polypeptides can also be identified by screening peptides for binding to RII. Random peptide sequences of at least about 14-amino acid residues that would be expected to form amphipathic helices can be identified by computer analysis, then screened for binding to RII by conventional methods, including, but not limited to, combinatorial chemistry and expression library approaches (e.g., phage expression libraries, including those in which a peptide is joined in reading frame to a outer structural protein of the phage). The Example below and Carr et al., *J. Biol. Chem.* 266:14188–14192, 1991, discuss various assays, e.g., an RII gel overlay procedure, that are useful for screening phage expression libraries for polypeptides that bind to RII.

AIPs are produced by standard techniques, preferably by chemical synthesis (see, e.g., Merrifield, *J. Amer. Chem. Soc.* 85:2149–2156, 1963). Alternatively, an AIP can be produced by standard genetic engineering techniques, i.e., by the expression of an AIP-encoding nucleic acid sequence in an appropriate host cell. The AIP may be expressed as a fusion polypeptide if binding to PKA is not significantly diminished by the fusion partner. For guidance regarding expression of polypeptides in various host cells, see, e.g., *Molecular Cloning: A Laboratory Manual*, 2nd ed., vol. 1–3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates).

Polypeptide Sequence Homology. Preferably, an AIP according to the present invention is at least about 70% homologous to a native AKAP polypeptide, preferably at least about 80% homologous, and more preferably at least about 95% homologous. Such homology is considered to be "substantial homology."

Polypeptide homology is typically analyzed using sequence analysis software such as the Sequence Analysis Software Package of the Genetics Computer Group, University of Wisconsin Biotechnology Center, Madison, Wis.).

"Isolated," "Purified," "Homogeneous" Polypeptides. A polypeptide is "isolated" if it has been substantially separated from contaminants, e.g., cellular components (nucleic acids, lipids, carbohydrates, and other polypeptides) that naturally accompany it. Such a polypeptide can also be referred to as "pure" or "homogeneous" or "substantially" pure or homogeneous. An AIP is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. See, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982.

AIPs Having a Non-native Sequence. Preferably, a modification to a natural AKAP sequence consists of a "conservative" amino-acid substitution. "Conservative" amino acid substitutions include those listed below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Non-conservative substitutions are those that reduce binding of an AIP to RII by at least about 50% as compared to an AIP having a sequence identical to that of a corresponding AKAP. Preferably, such substitutions reduce binding by 25% or less, and most preferably have no effect on binding or improve binding. Such non-conservative substitutions can result from changes in: (a) the structure of the AIP backbone in the area of the substitution; (b) the charge or hydrophobicity of the AIP; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; or (c) a residue having a bulky side chain, e.g., phenylalanine, is substituted for (or by) one not having a side chain, e.g., glycine. Preferably, a residue having an electropositive side chain, e.g., lysyl, arginyl, or histadyl, is not substituted for (or by) an electronegative residue, e.g., glutamyl or aspartyl.

Membrane-permeable AIPs. The present invention encompasses AIPs that are able to permeate cell membranes (e.g., sperm-cell membranes) and thus affect binding of PKA to an AKAP.

An AIP may be modified to include a fatty-acid moiety by conventional methods, preferably attached to either the amino terminus or the carboxy terminus of the peptide, most preferably to the amino terminus. Any fatty acid used in the art to achieve membrane-permeability of peptides may be employed, e.g., an N-stearylated peptide (Liotta et al., *J. Biol. Chem.* 269:22996–23001, 1994) or N-myristoylated peptide (O'Brian et al., *Biochem. Pharmacol.* 39:49–57, 1990; Eicholtz et al., *J. Biol. Chem.* 268:1982–1986, 1993).

Fatty acid-peptide conjugates have been used to inhibit protein kinase C (PKC) and tyrosine kinase activities in intact cells (Eichholtz et al., *J. Biol. Chem.* 268:1982–1986, 1993; Liotta et al., *J. Biol. Chem.* 269: 22996–23001, 1994).

AIPs according to the present invention may be introduced into cells by any conventional means. For example, an AIP may be incorporated into liposomes. Alternatively, the AIP can be formulated in a composition that includes an amphiphilic lipid, e.g., a head-to-tail amphiphile such as Lipofectin™ or a cationic facial amphiphile (CFA) (a conjugate of polyamines and bile-acid-based amphiphiles).

Preferably, the AIP is delivered in such a way that PKA activity is affected only or primarily in target cells, e.g., by topical application, by injection (e.g., into a joint to treat arthritis) or by cell- or tissue-specific delivery of the AIP by methods well known in the art.

Pharmaceutical Compositions Including AIPs

AIPs are useful for inhibiting sperm motility, and therefore for contraceptive purposes, as well as for other therapeutic or prophylactic purposes. Both human and veterinary uses are contemplated.

The present invention encompasses pharmaceutical compositions that include an "effective amount" of an AIP or mixture of AIPs and one or more non-toxic pharmaceutically acceptable carriers, excipient, diluents, and/or adjuvant. An "effective amount" of an AIP is an amount effective to substantially interfere with PKA binding to an AKAP, thereby causing a at least about a 50% reduction in PKA activity in a target cell, preferably at least about 75%, and most preferably at least about 90%. For contraceptive compositions, an "effective amount" of an AIP is an amount effective to diminish sperm motility by at least about 50%, preferably at least about 70%, more preferably at least about 80%, and most preferably at least about 90%.

The dosage rate, e.g., 0.05 to 20 mg/kg of body weight, is a function of the nature and body weight of the human or animal subject to be treated. The dosage unit involved depends, for example, on the condition treated, nature of the formulation, nature of the condition, embodiment of the claimed pharmaceutical compositions, mode of administration, and condition and weight of the patient, and the activity of a particular AIP. See, e.g., *The Pharmacological Basis of Therapeutics*, Goodman, Gilman, et al., eds., Macmillan, New York, 1994, and *Principles of Pharmacology*, Munson et al., ed., Chapman & Hall, NY, 1995. Standard pharmaceutical formulation techniques are used, such as those disclosed in *Remington's Pharmaceutical Sciences*, Mack Publishing Co., Easton, Pa., latest edition.

The pharmaceutical compositions or medicaments of the present invention can be formulated for administration by any of various routes. The compositions can be in the form of, for example, tablets, capsules, powders, granules, lozenges, dragees, pills, ampoules, suppositories, or liquid or gel preparations, such as oral, topical, or sterile parenteral solutions or suspensions. In the instance of contraceptives, the medicament is preferably formulated in a suppository, cream, foam, gel, or cream, for example, and placed in the vagina prior to intercourse, or applied to a condom, diaphragm, cervical cap, sponge, or other conventional contraceptive barrier.

Tablets and capsules for oral administration can be in a form suitable for unit-dose presentation and can contain conventional diluents and excipients. The pharmaceutical compositions will generally contain from 0.5 to 90% of the AIP by weight of the total composition. In addition to an AIP or combination of AIPs, the pharmaceutical compositions and medicaments can also contain other pharmaceutically active compounds.

For contraceptive use, an AIP or combination of AIPs may be combined with one or more other contraceptive substances, e.g., nonylphenoxy-polyethoxyethanol (nonoxynol-9), p-diisobutylphenoxy-polyethoxyethanol (octoxynol-9), gossypol, gramicidin, neem seed extracts (Praneem), reetha saponins, quinine hydrochloride, etc. Nonoxynol-9 and octoxynol-9 are surface-acting agents that disrupt the cell membrane and therefore can enable an AIP that is not otherwise membrane-permeable to inhibit sperm motility. A contraceptive composition combining an AIP and a nonoxynol-9, for example, may employ a lower level of nonoxynol-9 than if nonoxynol 9 is used alone, due to the contraceptive effect of the AIP. In addition to topical (female) contraceptives, systemic (male) contraceptives are also contemplated in which delivery of an AIP is targeted to an appropriate site to affect sperm motility.

Calcium at sufficient concentrations can overcome the sperm motility inhibition by an AIP. For that reason, a non-toxic chelating agent (such as EDTA or EGTA), or anion that combines with calcium ion to form an insoluble product, such as phosphate, can also be included.

Examples of conventional diluents and excipients include: binding agents such as syrup, acacia, gelatins, sorbitol, tragacanth, carboxymethyl cellulose and other cellulose derivatives, alginates, and polyvinylpyrrolidone; fillers and extenders such as sugars, starches, calcium phosphate, sorbitol, mannitol, salicic acid, or glycine; tableting lubricants, such as magnesium stearate, talc, polyethylene glycol or silica; disintegrants, such as potato starch; or acceptable wetting agents, such as sodium lauryl sulfatep; and diluents such as water, ethyl alcohol, isopropyl alcohol, ethyl carbonate, ethyl acetate, benzyl alcohol, benzyl benzoate, propylene glycol, 1,3-butylene glycol, dimethylformamide, oils (e.g., ground nut oil), glycerol, tetrahydrofurfuryl alcohol, polyethylene glycols, and fatty acid esters of sorbitol or mixtures thereof. Tablets can be coated by conventional methods.

Oral liquid preparations can be in the form of, for example, aqueous or oily suspensions, solutions, emulsions, syrups or elixirs, or can be presented as a dry product for reconstitution with water or other suitable vehicle before use. Such liquid preparations can contain conventional additives such as suspending agents, e.g., sorbitol, methyl cellulose, glucose, gelatin, or hydrogenated edible fats; emulsifying agents, e.g., lecithin, sorbitan monooleate, or acacia; non-aqueous vehicles, e.g., almond oil, fractionated coconut oil, oily esters such as glycerine, propylene glycol, or ethyl alcohol; preservatives such as methyl or propyl p-hydroxybenzoate or sorbic acid; and so forth.

Pharmaceutical compositions may also include additives, e.g., buffers such as sodium metabisulphite or phosphate buffers; preservatives such as bactericidal and fungicidal agents, including phenyl mercuric acetate or nitrate, benzalkonium chloride or chlorhexidine, thickening agents, such as hypromellose, or flavoring or coloring agents.

The pharmaceutical compositions can be applied topically. For topical application to the skin, the AIP can be made up into a cream, lotion, or ointment using conventional formulations. For topical applications to the eye, the AIP can be made up into a solution or suspension in a suitable sterile aqueous or non-aqueous vehicle.

The pharmaceutical compositions can also be administered parenterally in a sterile medium. The drug can be dissolved or suspended in the vehicle, depending on the vehicle or concentration used. Adjuvants such as local anesthetics, preservatives, and buffering agents can also be dissolved in the vehicle. Commonly used excipients for injectable forms of the pharmaceutical compositions of the present invention include physiological saline, Hank's solution, Ringer's solution, and the like. Injection can be, e.g., intravenous, intramuscular, intraperitoneal, or subcutaneous.

The claimed pharmaceutical compositions can also be administered by transdermal or transmucosal delivery by including agents which effect penetration of these tissues, such as bile salts, fusidic acid derivatives, cholic acid, and the like.

The invention will be better understood by reference to the following Example 9, which is intended to merely illustrate the best mode now known for practicing the invention. The scope of the invention is not to be considered limited thereto, however.

EXAMPLE

Materials and Methods

Sperm Preparation. Testes from mature bulls with intact tunica were obtained from a local slaughter house and sperm from caput or caudal epididymis were isolated and washed as previously described (Vijayaraghavan et al., *Biol. Reprod.* 32:489–500, 1985). The sperm were resuspended in buffer A (120 mM NaCl, 10 mM KCl, 10 mM Tris[hydroxymethyl] aminomethane (TRIS), pH 7.4) supplemented with 10 mM glucose and 10 mg/ml bovine serum albumin (BSA) for motility measurements. Monkey semen was obtained by electro-ejaculation and processed by procedures previously reported (Smith et al., *Biol. Reprod* 54:719–727, 1996). Human semen were obtained from a fertility clinic at the Oregon Health Sciences University.

Sperm Motility Measurement. Head motility parameters were determined as previously described (Vijayaraghavan et al., *Biol. Reprod* 54:709–718, 1996; Stephens et al., *Biol. Reprod.* 38:577–586, 1988). A 3–4 $\mu$L aliquot of sperm suspension ($5 \times 10^7$/ml) was loaded onto a counting chamber at 37° C. After bulk fluid movement had subsided, six different locations on the slide were recorded. The videotaped segments were analyzed by a computerized image-analysis system (CASMA) as previously described (Vijayaraghavan et al., *Biol. Reprod.* 54:709–718, 1996; Stephens et al., *Biol. Reprod.* 38:577–586, 1988). This computer system measures several parameters of head motion. In this report we have used Forward Motility Index (FMI) as a measure of motility. FMI is a product of percent motile (%M, percent of sperm moving at velocity greater than 20 mm/sec) and average velocity (Va, the five-point smoothed average of the head positions through at least 20 of the 30 frames analyzed). In most cases both components of FMI were found to increase together.

PKA Activity PKA was assayed as previously described (Carr et al., *J. Biol. Chem.* 268:20729–20732, 1993) with minor changes. Whole caput or caudal sperm were treated with 2-chloro-2-deoxyadenosine (50 $\mu$M), H-89 (50 $\mu$M), or both for 30 min. at 37° C. The sperm were then washed twice in ice cold homogenization buffer supplemented with protease inhibitors, benzamidine (10 mM), leupeptin (4 $\mu$g/ml), and N-tosyl-L-phenylalanine chloromethyl ketone (TPCK) (100 $\mu$M), and sonicated for one min. Reaction mixtures (20 uL total) contained 250 $\mu$M kemptide, 250 $\mu$M ($\gamma$-$^{32}$P)ATP, 25 mM Na$_3$VO$_4$, 50 mM 3-[N-morpholino]propanesulfonic acid (MOPS) (pH=7.0), 10 mM MgCl$_2$, 0.25 mg/ml BSA and where indicated, 10 $\mu$M cAMP. Assays were initiated by addition of labeled ATP, incubated for 2 min at 30° C., and stopped by addition of 30 $\mu$L of 1N HCl. Twenty $\mu$L of the reaction was then spotted on phosphocellulose paper followed by three washes in 75 mM phosphoric acid. The papers were then analyzed by Cerenkov counting. All determinations were in quadruplicates.

Preparation of Peptides with Thermal Fatty Acid. The peptides were synthesized on an automated synthesizer using 9-fluorenylmethoxycarbonyl (FMOC) chemistry employing base-mediated coupling. The activator of choice was either BOP or HATU using diisopropylethylamine as solvent. Stearic acid was added together with an activator of attachment to the free amino-terminus of the protected peptide. The progress of the stearation reaction was monitored by ninhydrin, a trifluoroacetic acid (TFA) test cleave, or by mass spectral or high-performance liquid chromatography (HPLC) analysis.

The final stearated peptide product was purified by reverse phase HPLC using a C8 column employing a TFA/acetonitrile buffer system. To identify the correct peak and facilitate recovery of pure material, the molecular weight confirmation of the stearated material was performed using a mass spectrometry analyzer. Analytical HPLC traces of the pooled fractions confirmed the expected purity. Pooled fractions were lyophilized to a dry powder under nitrogen. The peptides had the following sequences:

```
s-Ht31:    N-Stearate-DLIEEAASRIVDAVIEQVKAAGAY    (SEQ ID No. 9)

s-Ht31-P:  N-Stearate-DLIEEAASRPVDAVPEQVKAAGAY    (SEQ ID No. 10)

s-AKAP79:  N-Stearate-YETLLIETASSLVKNAIQLSIE      (SEQ ID No. 11)
```

Myristic acid could be used in place of the stearate.

Western blotting and overlay assays. The overlay procedure is a modified western blot procedure. Proteins were separated by SDS-polyacrylamide gel electrophoresis (SDS-PAGE) and transferred to a membrane (Immobilon, Millipore). After treatment with blotto (*Protein Methods*, Bollag and Edelstein, eds., Wiley-Liss, NY, 1991) to prevent non-specific binding, radiolabelled RIIα or RIIβ probes were applied (Carr and Scott, *Trends Biochem. Sci.* 17:246–249, 1992). Recombinant RIIα was produced as previously described (Carr et al., *J. Biol. Chem.* 266:14188–14192, 1991; Carr et al., *J. Biol. Chem.* 267:13376–13382, 1992). RIIα and RIIβ were gifts from Dr. John Scott, Oregon Health Sciences University, Portland, Oreg. Two different variations of the overlay assay were used. In the first, we used recombinant RII that has been radiolabeled by incubation with the catalytic subunit of PKA and $^{32}$P-ATP. After separation from free $^{32}$P-ATP, the $^{32}$P-RII (500,000 CPM/10 ml blotto) was incubated with the blocked blot for four hrs followed by washing and autoradiography. In the second procedure, the blot was incubated with cold RIβ (1 μg/10 ml blotto), washed, then incubated with anti-RIβ antiserum. After the blot was again washed, it was incubated with secondary antibody conjugated to horseradish peroxidase. A final wash was followed by development with an enhanced chemiluminescence kit (Renaissance™, New England Nuclear). The PKA isoform-specific antibodies were affinity-purified antibodies obtained from Triple Point Biologics, Forest Grove, Oreg.

Results

Identification of AKAPs and PKA isoforms in Bovine, Human and Monkey Sperm. Cyclic AMP is known to stimulate sperm motility in a variety of species. To determine if PKA anchoring is involved in regulating motility, we first identified the PKA isoforms and AKAPs present in mammalian sperm. Immunoblot analysis of sperm proteins with affinity-purified, isoform-specific antibodies detected three (RIIα, RIIβ, and RIβ) of the four known PKA isoforms in bovine, human and monkey sperm (Example 1A). No RIα was detected at the 50 to 55 kDa range in sperm from any of the species, even though RIα was detectable in bovine testis. The lower Mr bands detected in bovine and human sperm with anti-RIα antibody might be breakdown products of RIα. However, the other isoforms showed very little apparent proteolysis, suggesting these bands are probably due to the antibody cross-reacting with unrelated proteins. The fuzziness of the bands detected with the RIIα and RIβ antibodies suggest that these proteins may be at least partially phosphorylated.

To determine if these isoforms are associated with the soluble or insoluble fractions, bovine sperm were homogenized, centrifuged at 16,000×g for 30 min and subjected to western blot analysis (Example 1B). Greater than 50% of all three R subunit isoforms are present in the pellet fraction of sperm sonicates, and RIβ is found almost exclusively in this fraction. These results suggest that all of these isoforms are associated with structural or cytoskeletal elements of the sperm.

Overlay analysis of bovine, human and monkey sperm using $^{32}$P-labeled RIIα or RIIβ as probes detected a single dominant AKAP in each species (Example 1C). The bovine and human AKAP migrated at Mr 110,000 and the monkey AKAP was slightly larger at 115,000. The bands detected at approximately 55 kDa by the RIIβ probe are probably due to dimerization of the probe with endogenous RII, although it is not clear why these proteins are preferentially binding to RIIβ compared to RIIα. Overlay analysis using RIβ did not detect any binding proteins. These data suggest that a single AKAP in sperm may be responsible for the localization of both RIIα and RIIβ. The fact that RIβ is clearly present in the particulate fraction, but does not interact with denatured proteins on the blot, suggests that the overlay method may not be appropriate for detecting AKAPs that interact with RIβ. Instead, a non-denaturing binding assay, such as a band-shift assay (Carr and Scott, Trends Biochem. Sci. 17:246–249, 1992) may be used for detecting RI-binding proteins.

All AKAPs identified to date contain an amphipathic helix domain responsible for RII binding (Carr et al., *J. Biol. Chem.* 266:14188–14192, 1991; Carr et al., *J. Biol. Chem.* 267:13376–13382, 1992; Carr et al., *J. Biol. Chem.* 267:16816–16823, 1992; Coghlan et al., *J. Biol. Chem.* 269:7658–7665, 1994; McCartney et al., *J. Biol. Chem.* 270:9327–9333, 1995). A peptide, Ht31, containing an amphipathic helix domain, binds to RII and competitively inhibits the interaction of RII with other AKAPs (Carr et al., *J. Biol. Chem.* 267:13376–13382, 1992). Addition of this anchoring inhibitor peptide to the overlay assay blocked RII binding with AKAP 110 (Example 1D), suggesting that this sperm AKAP also contains an amphipathic helix-binding domain. A cell-permeable stearated Ht31 counterpart, S-Ht31, also inhibited in vitro binding of RII to AKAP 110, albeit at a reduced potency (85% inhibition compared with 100% by the non-stearated Ht31). The control peptide, S-Ht31-P, which has a proline substitution preventing amphipathic helix formation, had no affect on RII binding.

Effect of Anchoring Inhibitor Peptides (AIPs) on Sperm Motility. To determine if PKA anchoring affects sperm motility, S-Ht31 was added to vigorously motile sperm under a variety of conditions. S-Ht31 inhibits basal motility in a concentration- and time-dependent manner. Complete arrest of motility was observed at concentrations from 5 to 50 μM within three to five minutes after treatment (Example 2A). When motility is measured five minutes post-treatment, the concentration of S-Ht31 needed to produce 50% inhibition is approximately 1 μM (Example 2B). A control peptide, S-Ht31-P, which is ineffective in disrupting PKA anchoring to AKAPs (see Example 1D), had no effect on sperm motility at concentrations up to 20 μM, suggesting that motility inhibition by S-Ht31 was due to disruption of PKA anchoring.

To determine if S-Ht31 affects sperm viability or structural integrity, the vital dyes SYBR-green and rhodamine 123 were added to sperm before and after treatment with S-Ht31. Only viable, intact cells take up these dyes. Both treated and control sperm accumulated these dyes to the same extent, suggesting that the stearated peptide did not decrease viability or disrupt the integrity of the sperm plasma membrane. In experiments using sperm loaded with the chromophores BCECF or Fura 2, addition of digitonin, but not S-Ht31, caused release of these dyes, confirming that peptide treatment did not compromise the integrity of the plasma membrane.

Perhaps the best evidence supporting the viability of the S-Ht31 treated sperm is that, under certain conditions, the sperm are able to regain full motility. Monitoring motility beyond five minutes of S-Ht31 treatment showed that sperm kinetic activity recovered spontaneously over 30 to 60 minutes (Example 3A). Recovery of activity occurred only in sperm suspended in calcium-containing media. In medium depleted of external calcium by EGTA, S-Ht31 caused irreversible motility arrest. The motility of untreated sperm was unaffected in the presence or absence of calcium.

Bicarbonate ion has been shown to stimulate sperm adenylyl cyclase (Okamura et al., *J. Biol. Chem.* 260:9699–9705, 1985) increase intracellular pH (Vijayaraghavan et al., *Biol. Reprod.* 32:489–500, 1985) and is an essential component of suspension buffers required for optimal sperm function in vitro (Lee and Storey, *Biol. Reprod.* 34:349–356, 1986; Kopf and Gerton, in *Elements of Mammalian Fertilization*, Wassarmaan, ed., pp. 153–203, CRC Press, Boca Raton, Fla., 1991). Sperm motility in the presence of bicarbonate is significantly enhanced compared to untreated sperm (Example 3B). To determine the effect of AIPs on optimal motile sperm, S-Ht31 was added to sperm in both basal and bicarbonate-supplemented media (Example 3B). The peptide was equally effective in inhibiting motility in both media. Similar results were obtained when sperm were pretreated with other activators of motility, dibutyryl cyclic$^{3'5'}$ adenosine monophosphate (db-cAMP), isobutylmethyl-xanthine (IBMX), and CDA, all thought to increase cAMP content.

In similar experiments, the AIPs also caused inhibition of motility when added to undiluted rhesus monkey (Examples 6 and 7) and human ejaculated semen (Example 8).

Role of PKA in sperm motility and S-Ht31 action. If the effect of anchoring inhibitor peptides on sperm motility is due to the dissociation of the catalytic subunit of PKA from its preferred substrates, then this effect should be mimicked by inhibitors of PKA activity. To test this hypothesis, we studied the effect of a potent cell permeable PKA inhibitor on sperm motility. Addition of high levels of H89 (50 $\mu$M) inhibited basal sperm motility approximately 50% or less, and had no effect on sperm motility stimulated by the adenosine analog 2-chloro-2-deoxyadenosine (CDA) (Example 4A). Essentially identical data was obtained when sperm were stimulated with IBMX or 8-bromo-cAMP (8-Br-cAMP) instead of CDA. This unexpectedly weak action of H-89 apparently results primarily from a decrease in motility of a subpopulation of sperm, because a considerable proportion of sperm maintain vigorous motility. This contrasts sharply with the complete arrest of motility seen in S-Ht31 treated sperm. Also, unlike the action of AIPs, the effects of H-89 were strongly suppressed by CDA. The effectiveness of H-89 was also observed with caput sperm, which are immotile unless stimulated with agents such as CDA or IBMX. Motility induction by CDA is unaffected by preincubating sperm with H-89 before treatment (Example 4A). Together these observations suggest that AIPs and PKA inhibitors have different mechanisms of action.

In previous reports, initiation or stimulation of sperm motility by CDA was associated with an elevation of cAMP and an increase in PKA activity was assumed (Vijayaraghavan and Hoskins, *Biol. Reprod.* 34:468–77, 1986). Because H-89 failed to suppress stimulation of motility by CDA, we measured PKA activity from caudal and caput sperm which had been treated with CDA, H-89 or CDA plus H-89 (Example 4B). All assays were performed in the absence or presence of cAMP to determine the basal and maximal PKA activities. CDA increased basal PKA activity by approximately 60% in both caudal and caput sperm. H89 treatment, in the presence or absence of CDA, strongly inhibited PKA activity. Addition of cAMP to the assay was not able to overcome this inhibition. To insure that H-89 was affecting PKA activity in the cells and not just its activity in the in vitro assay, the sperm were washed several times before lysis to remove all exogenous H-89. As a control, a non-permeable PKA inhibitor, PKItide (50 $\mu$M) was added to sperm. The sperm were then washed, lysed and assayed for PKA activity in a manner identical to the H-89 treated sperm. PKItide had no effect on cellular PKA activity, although a similar concentration, when added to the PKA assay, will inhibit virtually 100% of activity. These data suggest that motility stimulation associated with treatments that elevate cAMP does not require increases in the catalytic activity of PKA and can occur even if PKA activity is substantially inhibited.

Discussion

As an initial step in studying the role of PKA anchoring in regulation of sperm function, we first identified PKA isoforms and AKAPs that are present in mammalian sperm. Three of the four isoforms of the regulatory subunit of PKA were detected in bovine, human and monkey sperm. RI$\alpha$, though abundant in testis, was not detected in sperm. Consistent with previous reports (Horowitz et al., *J. Biol. Chem.* 263:2098–2104, 1988), the major proportion of all isoforms remained in the particulate fraction, presumably due to their interaction with AKAPs. Bovine, human and monkey sperm all contain one predominant AKAP with a relative molecular weight of 110,000 to 115,000. The AKAPs predominately localize to the particulate fraction and bind both RII$\alpha$ and RII$\beta$, suggesting that a single AKAP is responsible for the localization of both these RII isoforms. Overlay assays using RI$\beta$ as a probe did not detect any binding protein in sperm. Preliminary analysis by electron microscopy detects RII$\beta$ in both the head and tail, while RII$\alpha$ is almost exclusively associated with the axoneme.

In accord with our observations, Orr and colleagues reported one predominant AKAP at an Mr of approximately 120,000 in bovine sperm (Horowitz et al., *J. Biol. Chem.* 263:2098–2104, 1988), and Rubin and colleagues found a single RII$\beta$ AKAP (~120 kDa) in mature mouse sperm (Lin et al., *J. Biol. Chem.* 270:27804–27811, 1995). Others, however, have reported RII$\alpha$ AKAPs of 82 kDa in mouse (Carrera et al., *Dev. Biol.* 165:272–284, 1994), 80 kDa in rat (Horowitz et al., *J. Biol. Chem.* 263:2098–2104, 1988) and 72 kDa in human (Pariset and Weinman, *Mol. Reprod. Develop.* 39:415–422, 1994). The reason for these differences is not clear, although proteolysis is one possibility. We find that prolonged storage of SDS-solubilized extracts leads to the loss of the 110-kDa band and the appearance of an 80-kDa band. The 72-kDa RII$\alpha$-binding band reported in human sperm (Pariset and Weinman, *Mol. Reprod. Develop.* 39:415–422, 1994) is distinct from all other known AKAPs due to the fact that it was detected using a peptide from RII$\alpha$ (amino-acid residues 45–75) which does not contain the AKAP-binding domain (Luo et al., *J. Biol. Chem.* 265:21804–21810, 1990; Scott et al., *J. Biol. Chem.*

265:21561–21566, 1990; Hausken et al., *J. Biol. Chem.* 269:24245–24251, 1994; Li and Rubin, *J. Biol. Chem.* 270:1935–1944, 1995). Finally, the cloning of a sperm AKAP of 84 kDa that is uniquely expressed during spermatogenesis has been reported (Lin et al., *J. Biol. Chem.* 270:27804–27811, 1995). This AKAP is not found in mature sperm and thus its relationship, if any, to AKAP 110 in mature sperm is unknown. To date, only sperm cells have been shown to contain an AKAP of 110 kDa.

Flagellar activity in sperm is regulated by cAMP (Tash, *Cell Motil. Cytoskel.* 14:332–339, 1989; Garbers and Kopf, in *Advances in Cyclic Nucleotide Research*, Greengard and Robison, eds., Vol. 13, pp. 252–306, Raven Press, New York, 1980; Lindemann and Kanous, *Arch. Androl.* 23:1–22, 1989; Tash and Means, *Prog. Clin. Biol. Res.* 267:335–355, 1988). Both PKA and AKAPs have been shown to be located at the same subcellular site in sperm, the outer mitochondrial membrane located on the proximal flagella (i.e., the sperm "midpiece") (Lieberman et al., *J. Cell Biol.* 107:1809–1816, 1988; Lin et al., *J. Biol. Chem.* 270:27804–27811, 1995). Our study is the first to investigate the role of subcellular PKA anchoring in sperm function. Addition of a cell permeable anchoring inhibitor peptide dramatically inhibits sperm motility in a dose- and time-dependent manner. This inhibition is reversible, but only in the presence of external calcium, suggesting that the regulatory mechanism being disrupted may involve maintenance of calcium homeostasis or a calcium regulated function that recovers only in the presence of exogenous calcium. Since mitochondria play an important role in sperm calcium homeostasis (Babcock et al., *J. Biol. Chem.* 251:3881–3886, 1976; Vijayaraghavan and Hoskins, *Cell Calcium* 10:241–253, 1989; Vijayaraghavan et al., *Biol. Reprod.* 40:744–751, 1989; Vijayaraghavan and Hoskins, *Mol. Reprod. Develop.* 25:186–194, 1990; Vijayaraghavan et al., *Mol. Reprod. Dev.* 38:326–333, 1994), it is reasonable that disruption of RII anchoring in this region could be responsible for the changes in sperm $Ca^{2+}$ regulation. The control peptide, S-Ht31-P, had no effect on motility, suggesting that motility inhibition by S-Ht31 was not due to the stearate moiety but due to disruption of PKA anchoring. Reversibility of the motility inhibition and the observations that S-Ht31 treated sperm take up vital dyes provide evidence that the motility inhibition is not due to disruption of sperm plasma membrane integrity. The simplest model consistent with these data is that the interaction of the regulatory subunit of PKA with AKAP 110 is essential for sperm movement.

It is usually assumed that the main function of this interaction is to anchor the catalytic subunit at a preferential subcellular site for specific phosphorylation of protein substrates in the vicinity. This model is supported by studies showing that microinjection of anchoring inhibitor peptides (AIPs) into neuronal or muscle cells mimics the effect of PKA inhibitors causing loss of cAMP modulation of the glutamate receptor and voltage gated Ca channels (Rosenmund et al., *Nature* 368:853–856, 1994; Johnson et al., *Proc. Natl. Acad. Sci. USA* 91:11492–11496, 1994). We find, however, that in sperm, inhibition of the catalytic subunit of PKA does not mimic the effect of AIPs, suggesting that the interaction of the regulatory subunit with sperm AKAPs has regulatory actions independent of the catalytic subunit. Others have also suggested that the regulatory subunit acts independently of the catalytic subunit (De Camilli et al., *J. Cell Biol.* 103:189–203, 1986). It is known that RII can inhibit phosphatases (Khatra et al., *Biochem. Biophys. Res. Commun.* 130:567–573, 1985) and preliminary data from our lab show that RII will inhibit sperm PP1. An independent role of RII in the regulation of sperm motility has also been suggested by reports showing that the addition of axokinin (later shown to be RII [Noland et al., *Biol. Reprod.* 37:171–180, 1987; Paupard et al., *J. Cell Biochem.* 37:161–175, 1988]) to demembraned sperm was sufficient to induce motility (Tash et al., *Cell* 38:551–559, 1984; Tash et al., *J. Cell Biol.* 103:649–655, 1986; Tash and Bracho, *J Androl.* 15:505–509, 1994).

Even though the activation of motility agents which increase sperm cAMP is well substantiated, the role of PKA has never been clear. For instance, PKA inhibitors reportedly do not alter the stimulatory actions of cAMP on motility of intact or demembranated sperm (Carr and Acott, *Biology of Reproduction* 43:795–805, 1990; San Agustin and Witman, *Cell Motility & the Cytoskeleton* 27:206–18, 1994). These reports, however, did not conclusively establish that the PKA inhibitors were indeed inhibiting sperm PKA. Our studies now document that under conditions where sperm PKA is clearly inhibited, compounds that elevate cAMP such as CDA, IBMX, and 8-Br-cAMP still induce or stimulate sperm motility. The lack of effect of H-89, even at concentrations as high as 50 $\mu$M, on cAMP-mediated induction and stimulation of motility is quite unequivocal. Our data suggest that the association of RII with AKAPs, but not PKA catalytic activity, is required for sperm motility. Therefore, RII, independent of PKA activity, may regulate other biochemical events such as phosphatase activity and intracellular ion concentration.

This regulation may involve protein-protein interaction between the RII/sperm AKAP complex and other sperm proteins. The demonstration that the phosphatase PP2B, PKA, and PKC are all anchored to the same AKAP in neurons (Klauck et al., *Science* 271:1589–1592, 1996) opens up several possible, previously unidentified, roles for the individual members of this multimeric complex. The interaction between RII and other sperm proteins could also be cAMP-dependent, since cAMP is known to produce a conformational change in the regulatory subunit. Our data shows that RII anchoring, independent of PKA catalytic activity, is essential for sperm motility and that cell-permeable AIPs disrupt PKA anchoring and cellular function.

All publications and published patent documents cited in this specification are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. All modifications that are within the spirit and scope of the invention are to be included within the scope of the invention as described herein.

We claim:

1. A pharmaceutical composition comprising:
   an effective contraceptive amount of a synthetic peptide fatty acid conjugate comprising an amphipathic α-helix domain that binds to an RII subunit of protein kinase A, and competitively inhibits binding of protein kinase A to sperm A kinase anchoring proteins; and
   a pharmaceutical carrier.

2. The composition of claim 1, wherein the pharmaceutical carrier is suitable for intravaginal delivery of the contraceptive amount of the synthetic peptide.

3. The composition of claim 1, wherein the synthetic peptide is selected from the group consisting of SEQ ID NOS: 1, 2, 3, 4, 5, 6, 7, 8, 9, 10, and 11.

4. The composition of claim 1 further comprising a spermicidal agent.

5. The composition of claim 4, wherein the spermicidal agent is selected from the group of nonoxynol-9, octoxynol-9, gossypol, gramicidin, neem seed extracts, reetha saponis, and quinine hydrochloride.

6. The composition of claim 2, wherein the composition is in the form of a suppository, cream, foam or gel.

7. A method of inhibiting sperm motility, comprising exposing the sperm to an effective amount of a synthetic anchor inhibiting peptide fatty acid conjugate comprising an amphipathic α-helix domain that binds to an RII subunit of protein kinase A, and competitively inhibits binding of protein kinase A to sperm A kinase anchoring protein.

8. The method of claim 7, wherein the peptide is a cell permeable peptide.

9. The method of claim 8, wherein the fatty acid comprises myristate.

10. The method of claim 7, wherein the peptide is incorporated into a pharmaceutical composition, and introduced into a vagina.

11. The method of claim 10, wherein the synthetic peptide is selected from the group consisting of SEQ ID NOS: 1, 2, 3, 4, 5, 6, 7, 8, 9, 10, and 11.

12. The method of claim 10, wherein the pharmaceutical composition is a suppository, foam, cream or gel.

13. The method of claim 10, wherein the pharmaceutical composition is placed in the vagina prior to sexual intercourse.

14. A pharmaceutical composition comprising an effective contraceptive amount of a synthetic peptide selected from the group consisting of SEQ ID NOS: 1, 2, 3, 4, 5, 6, 7, 8, 9, 10, 11, and conservative variants thereof, which competitively inhibit binding of protein kinase A to sperm A kinase anchoring proteins.

* * * * *

SEQUENCE LISTING

<160> NUMBER OF SEQ ID NOS: 11

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Leu Ile Glu Glu Ala Ala Ser Arg Ile Val Asp Ala Val Ile
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Thr Ala Glu Glu Val Ser Ala Ile Arg Val Gln Val Val Thr
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Leu Ile Glu Thr Ala Ser Ser Leu Val Lys Asn Ala Ile Gln
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Leu Ile Glu Thr Ala Ser Ser Leu Val Lys Asn Ala Ile Glu
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Glu Val Ala Ala Glu Val Leu Ala Glu Val Ile Thr Ala Ala Val Lys
 1               5                  10                  15

Ala Val

<210> SEQ ID NO 6
<211> LENGTH: 14
<212> TYPE: PRT

<213> ORGANISM: Artificial Sequence
<220> FEATURE:
<223> OTHER INFORMATION: Description of Artificial Sequence: synthetic
      peptide

<400> SEQUENCE: 6

Ile Ile Asp Met Ala Ser Thr Ala Leu Lys Ser Lys Ser Gln
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Leu Ala Glu Lys Ile Val Ala Glu Ala Ile Glu Lys Ala Glu
 1               5                  10

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Val Ile Ser Glu Ala Thr Glu Gln Val Leu Ala Thr Thr Val Gly Lys
 1               5                  10                  15

Val Ala Gly Arg Val Cys
             20

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Asp Leu Ile Glu Glu Ala Ala Ser Arg Ile Val Asp Ala Val Ile Glu
 1               5                  10                  15

Gln Val Lys Ala Ala Gly Ala Tyr
             20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Asp Leu Ile Glu Glu Ala Ala Ser Arg Pro Val Asp Ala Val Pro Glu
 1               5                  10                  15

Gln Val Lys Ala Ala Gly Ala Tyr
             20

<210> SEQ ID NO 11
<211> LENGTH: 22
<212> TYPE: PRT
<213> ORGANISM: Artificial Sequence

```
-continued

<220> FEATURE:
<223> OTHER INFORMATION: Description of Artificial Sequence: synthetic
      peptide

<400> SEQUENCE: 11

Tyr Glu Thr Leu Leu Ile Glu Thr Ala Ser Ser Leu Val Lys Asn Ala
 1               5                  10                  15

Ile Gln Leu Ser Ile Glu
            20
```